United States Patent [19]

Lehneis

[11] 4,220,148
[45] Sep. 2, 1980

[54] KNEE STABILIZER

[75] Inventor: Hans R. Lehneis, Massapequa Park, N.Y.

[73] Assignee: New York University, New York, N.Y.

[21] Appl. No.: 872,640

[22] Filed: Jan. 26, 1978

[30] Foreign Application Priority Data

Feb. 12, 1977 [DE] Fed. Rep. of Germany ....... 2705978

[51] Int. Cl.$^2$ .......................... A61F 3/00; A61F 15/00
[52] U.S. Cl. .................................................. 128/80 C
[58] Field of Search ................. 128/80 C, 80 B, 80 R, 128/80 F, 88, 165; 2/22, 24

[56] References Cited

U.S. PATENT DOCUMENTS

| | | | |
|---|---|---|---|
| 1,517,915 | 12/1924 | Masland | 128/88 |
| 2,144,641 | 1/1939 | Snyder | 128/80 C |
| 2,195,024 | 3/1940 | Bullock | 128/88 |
| 2,460,895 | 2/1949 | Meany | 128/80 C |
| 3,026,869 | 3/1962 | Peach | 128/80 F |
| 3,194,233 | 7/1965 | Peckham | 128/80 C |
| 3,719,187 | 3/1973 | Ulansey | 128/87 R |
| 3,785,372 | 1/1974 | Craig | 128/84 R |
| 3,786,804 | 1/1974 | Lewis | 2/24 |
| 4,111,194 | 9/1978 | Cox et al. | 128/80 C |

FOREIGN PATENT DOCUMENTS 544634 2/1932 Fed. Rep. of Germany ........ 128/80 C

*Primary Examiner*—Robert W. Michell
*Assistant Examiner*—Arthur S. Rose
*Attorney, Agent, or Firm*—Darby & Darby

[57] ABSTRACT

A knee stabilizer or brace is provided which is useful as an aid for patients having any of the three common forms of knee joint deformation. The brace includes a pair of guide rails which extend along the patient's leg on either side of the knee. An upper cross-member, which is contoured to fit the front of the patient's thigh, is mounted for pivotal movement near the top of each guide rail. The upper cross-member is retained on the patient's thigh by means of an elastic band which extends around the rear of the thigh and, at either end, is secured to the upper cross-member. A medial cross-member, which is shaped to fit the contour of the patient's calf, is pivotally mounted to each of the guide rails intermediate its ends and engages the patient's leg at a point near the knee joint. Near the bottom of one of the guide rails and facing the front of the patient's leg, a strap loop is provided and an adjustable strap, which is secured to the other guide rail, passes through the loop so as to extend across the patient's shin, and to loop back on itself and is secured to itself. With the brace on the patient's leg, the maximum extension of the knee is conveniently regulated by adjusting the shin strap while his leg is fully extended. Thereafter, the cross-members and strap cooperate to prevent overextension of the knee joint. Owing to the pivotal mounting of the upper and medial cross-members, the brace may be fitted closely to the patient's leg, thereby providing better lateral stabilization of the knee joint and a slip-proof fit, and rendering the brace undetectable under the clothing.

13 Claims, 5 Drawing Figures

KNEE STABILIZER

The invention relates to a brace for providing support to and preventing straining of the knee.

Various nervous, muscular, ligament and bone disorders can lead to deformities in a patient's knee joint. For example, bone arthritis may result in weakening of the knee ligaments due to inflammation. Frequently, the ligaments at a particular location in the joint are weakened with respect to the opposed ligaments and distortion of the leg results. Thus, the conditions commonly known as back-knee (rearward arching or overextension at the joint), knock-knee (inward arching at the joint) and bow-leggedness (outward arching at the joint) result from weakening of the rear, inner and outer ligaments, respectively, with respect to the opposing ligaments. Although these conditions are not generally curable, artificial correction by providing mechanical stabilization and support could relieve the pain which often accompanies such knee joint distortions and could halt further deterioration of or injury to the joint.

In an article titled "The Swedish Knee Cage," in the Journal "Artificial Limbs," Vol. 12, No. 2, pp. 54–57, Autumn 1969, a knee brace is described which consists of two uprights, one along each side of the knee, respectively, interconnected, as explained below, by means of several bands of webbing and a rigid cross-member. At the upper and lower ends of the uprights, bands are affixed between the uprights so as to lie on the front of the thigh and shin bone, respectively. Accurate fit of the bands is obtained by snap buttons adjusting the length of the bands and by the resilience of the bands themselves. At the level of the knee-joint, the two uprights are firmly interconnected by a semicircular rigid cross-member, and a third band, which is between the cross-member and leg, is forced against the rear of the knee-joint, thereby preventing its over-extension.

With this prior art knee-brace, it has been found especially disadvantageous that the bands, especially those which lie on the front of the thigh and shin bone, do not fit accurately when the knee is bent, but stand away. Thus, the knee brace moves easily and the bands protrude from the leg and are distinctly visible through the clothing—pants or skirt—in an undesirable fashion. The movement of the brace also results in its slipping downward on the leg and necessitates its adjustment when the Patient stands up. This can prove very inconvenient.

Another disadvantage of the prior art brace is that it offers no lateral support for the knee joint and is, therefore, useful only for patients having back-knee distortion. In addition, the prior art device can only be adjusted for fit in discreet steps, with the result that the precise fit for each patient's needs can not be achieved.

Broadly, it is an object of this invention to provide a brace for stabilizing and supporting the knee joint to prevent strain and deformation. Specifically, it is contemplated that the brace be useful in treating all three common types of deformation mentioned above.

It is another object of the invention to provide a knee-stabilizing brace which provides lateral support and a snug fit on the patients leg throughout its entire range of movement, yet does not interfere with that movement.

It is yet another object of the invention to provide a knee brace which is readily adjustable by the Patient over a continuous range in order to achieve perfect fit and operation.

It is a further object of the invention to provide a knee brace which is sturdy, reliable and convenient in use, yet relatively simple and inexpensive in construction.

In accordance with an illustrative embodiment demonstrating objects and features of the present invention, a knee brace is provided which is useful as an aid for patients having any of the three common forms of knee joint deformation. The brace includes a pair of guide rails which extend along the patient's leg on either side of the knee. An upper cross-member, which is contoured to fit the front of the patient's thigh, is mounted for pivotal movement near the top of each guide rail. The upper cross-member is retained on the patient's thigh by means of an elastic band which extends around the rear of the thigh and, at either end, is secured to the upper cross-member. A medial cross-member, which is shaped to fit the contour of the patient's calf, is pivotally mounted to each of the guide rails intermediate its ends and engages the patient's leg at a point near or below the knee joint. Near the bottom of one of the guide rails and facing the front of the patient's leg, a strap loop is provided and a heavy, adjustable strap, which is secured to the other guide rail passes through the loop so as to extend across the patient's shin and to loop back on itself and is secured to itself.

In practice, the guide rails are shaped to follow the profile of the patient's leg and may, therefore, be mounted in intimate contact with the leg. With the brace on the patient's leg, the maximum extension of the knee is conveniently regulated by adjusting the shin strap while his leg is fully extended. Thereafter, the pressure provided at the rear of the leg by the medial cross-member and at the front of the leg by the upper cross-member and the adjustable strap cooperate to prevent overextension of the knee joint (i.e. back knee). Owing to the pivotal mounting of the upper and medial cross-members, the brace may be fitted closely to the patient's leg, thereby providing better support and a slip-proof fit, and rendering the brace undetectable under the clothing.

The foregoing brief description, as well as further objects, features and advantages of the invention will be understood more completely from the following detailed description of presently preferred, but nonetheless illustrative, embodiments of a knee brace in accordance with the present invention, with reference being had to the drawings, in which.

Figure 1:
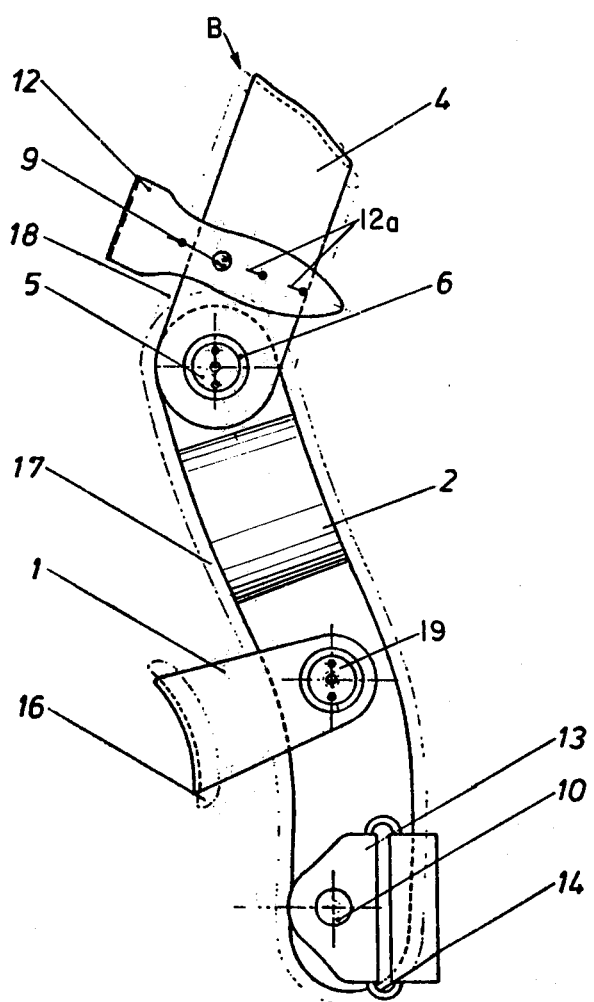
FIG. 1 is a side elevational view of a first embodiment of a knee brace in accordance with the present invention.
Figure 2:
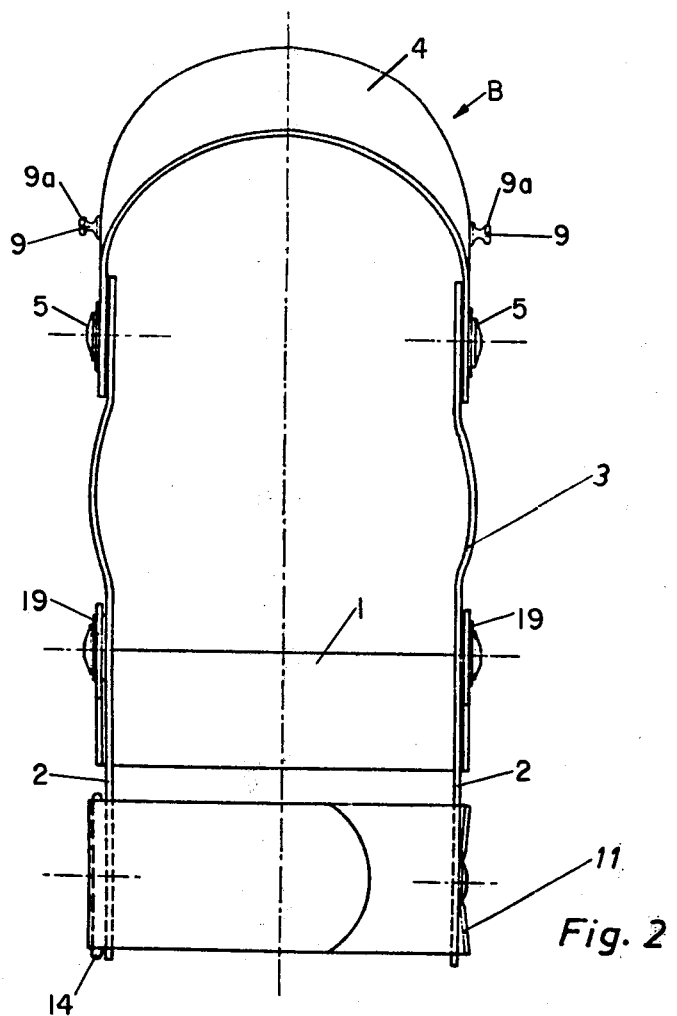
FIG. 2 is a front elevational view of the knee brace of FIG. 1.
Figure 3:
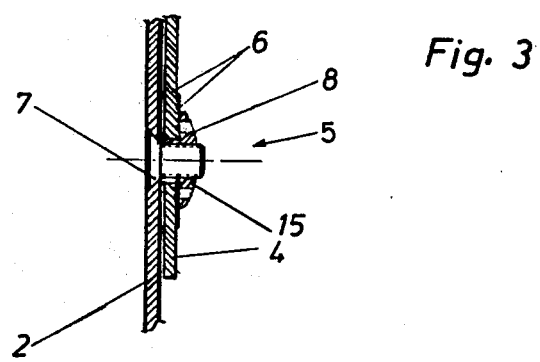
FIG. 3 is a sectional view, on an enlarged scale, showing a preferred joint connection employed in the knee brace.

Referring now to the details of the drawing, FIGS. 1–3 illustrate a first illustrative embodiment B of a knee brace in accordance with the present invention. The brace is adapted to be mounted on the leg of a patient (see FIGS. 4 and 5) in order to prevent the three most common forms of knee joint distortion, namely, backknee, knock-knee and bow-leggedness.

The brace B broadly comprises: a pair of guide rails 2, which are adapted to engage the leg on either side and to extend above and below the knee joint; a medial cross-member 1 pivotally mounted intermediate the ends of guide rails 2; an upper cross-member 4 pivotally mounted near the tops of guide rails 2, and an adjustable strap 11 connected between the lower ends of guide rails 2 in a position to engage the patient's shin.

The guide rails 2 are preferably made from a light metal covered with a plastic material which may be flesh-colored. However, it will be apparent to those skilled in the art that other materials may be used for this purpose and will provide adequate stiffness and firmness for the required structural strength, as well as the formability required for comfort and inconspicuous wear. The cross-members may be made of similar materials. As can be seen in FIG. 2, guide rails 2 are slightly S-shaped to conform to the profile of an extended leg and are also somewhat bowed at 3 (see FIG. 3) to conform to the contour of the knee joint. This bowing may also be adjusted to permit the guide rails to fit snugly against the sides of a leg with a swelled knee joint (such swelling is common in arthritic joints) so as to provide firm lateral stabilization and support. The inner surfaces of the guide rails 2, which face the patient's leg, are provided with padding 17. This adds to the patient's comfort, provides close conformity with the leg, and resists upward and downward slippage of the guide rails.

The upper cross-member 4 is mounted near the top of each of the guide rails 2 by means of a hinge joint 5 which permits relative pivotal movement between cross-member 4 and guide rails 2. Cross-member 4 is a rigid strip which is bent into a curved shape and has a tapered surface, so that it may be rested against the front of the patient's thigh and will closely conform thereto. The inner surface of cross-member 4 is provided with padding 18 similar to padding 17 of guide rails 2. At a distance from each of the hinged joints 5, cross-member 4 includes an outwardly extending lug 9 to which an elastic band 12 is secured. Securement of the elastic band is achieved by means of a number of aligned slits 12a, resembling button holes, which extend inwardly from either end of band 12. Each end of the band is secured to cross-member 4 by inserting the enlarged head 9a of one of the lugs 9 into one of the slits 12a near that end. The band 12 functions to draw cross-member 4 towards the leg, thereby preventing brace B from slipping down on the patient's leg, as will be explained more completely below.

The medial cross-member 1 is mounted to each of guide rails 2 intermediate its ends by means of a hinge joint 19 which permits relative pivotal movement between cross-member 1 and guide rails 2. Cross-member 1 is a rigid strip which is bent into a curved shape and has a slightly curved surface, so that it may be rested against the upper part of the patient's calf and will closely conform thereto. The pivotal mounting of the medial cross-member and its close conformity to the calf permit increased maneuverability for the patient's leg while retaining a firm fit. In existing knee braces, for example the one discussed above, maneuverability is possible only within the range of flexibility of the bands and padding. On the internal surface facing the patient's calf, cross-member 1 may contain padding 16 similar to padding 17 of guide rails 2.

Strap 11, in effect, forms a lower cross-member which passes across the patient's shin. Referring to FIG. 2, it will be observed that strap 11 is secured at the lower end of the right-hand one of guide rails 2, for example, by being riveted. At a corresponding point on the other guide rail, strap guide loop 14 is mounted in retaining means 13, which is secured near the lower end of the left hand one of guide rails 2, for example, by means of a rivet (see FIG. 1). The free end of strap 11 is passed through guide loop 14 and is then looped back on itself. The two surfaces of strap 11 which are brought into contact by this looping back are provided with complementary fastening surfaces which permit the belt to be secured in its looped back position. In the preferred embodiment, the surfaces of the belt are provided with mating surfaces of the material sold under the name of "Velcro" by the American Velcro Company. These mating surfaces permit continuous adjustment of the length of the portion of strap 11 extending between guide rails 2. This, in turn, permits continuous adjustment of the maximum extension of the knee joint, as will be explained more fully below.

It will be appreciated that, as an alternative to the foregoing strap construction, each of guide rails 2 may be provided with a guide loop 14. Strap 11 may then be a length of flexible strap with complementary fastening surfaces on its two faces and it may then be passed through both guide loops 14 and folded back and secured to itself to form a closed loop. Thus, the strap is adjusted by adjusting the size of its closed loop.

FIG. 3 illustrates the preferred construction of hinge joints 5 which are identical to hinge joints 19. Pivoting in the joints 5 takes place about the shaft of a screw 7 which extends through aligned holes in a corresponding guide rail 2 and upper cross-member 4. Screw 7 is provided with a tapered, flat head and the hole in guide rail 2 which receives the head is countersunk to permit flush mounting thereof. The shaft of screw 7 extends through the hole in guide rail 4 and receives a nut 15, by means of which the hinge joint 5 is tightened. Sliding discs 6 and bearing sleeve 8 are provided to permit cross-member 4 to pivot independently of guide rail 2 and screw 7 and to stabilize the hinge joint. This results in a hinge joint which is compact and free of unnecessary looseness, but which rotates very smoothly.

Figure 4:
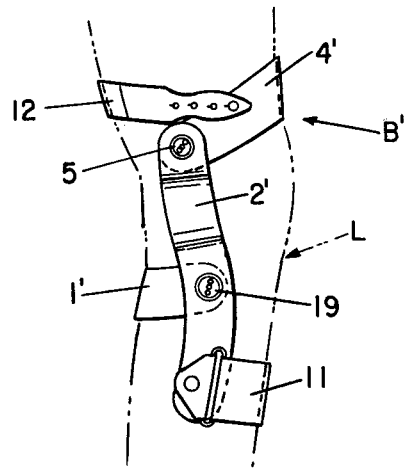
FIG. 4 is a side elevational view of a second embodimentof the knee brace in accordance with the present invention, the brace being shown on a patient's leg with the leg in an extended position.
Figure 5:
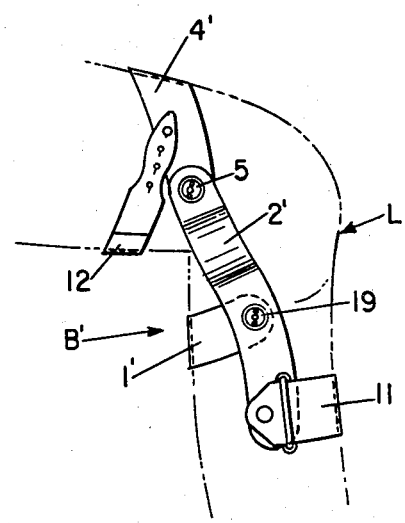
FIG. 5 is a side elevational view of the knee brace of FIG. 4 shown on the leg of a patient with the leg in a bent position.

Referring to FIGS. 4 and 5, there is shown an alternate embodiment B' of a knee brace in accordance with the present invention. The brace B' is substantially identical to the brace B, the primary distinction being that the cross-members 1' and 4' are mounted under the guide rails 2' (as seen in FIG. 4), whereas the cross-members 1 and 4 are mounted over the guide rails 2 (as seen in FIG. 1).

The function and operation of the brace B' will now be described with the aid of FIGS. 4 and 5. However, it will be appreciated that the same description applies equally well to brace B. The brace B' is applied to the patient's leg L so that one of the guide rails 2' extends along each side of the leg and also extends above and below the patient's knee joint. With the knee brace so applied, upper cross-member 4' extends across the front of the patient's thigh, medial cross-member 1' extends across the patient's calf at a point just below the knee joint, and strap 11, also a cross-member when closed, extends across the patient's shin.

Strap 12 is joined to upper cross-member 4' at a distance from the hinge joint 5 and therefore tends to exert a force on the cross-member which tends to rotate it counterclockwise. Thus, elastic band 12 cooperates with upper cross-member 4' to form a closed elastic loop which is retained in a fixed position on the patient's thigh. This prevents the brace B' from shifting downward on the patient's leg and avoids the repeated adjustment that was required in the prior art knee braces.

The brace is initially adjusted by the patient by extending his leg to the desired maximum extension and then fastening of the strap 11 on itself. Thereafter, extension of the patient's leg beyond the point of adjustment will be prevented by the forces applied at the front of the leg by upper cross-member 4' and strap 11 and at the rear of the leg by medial cross-member 1'.

When the patient's leg is bent (see FIG. 5) upper cross-member 4' is still securely retained on the patient's thigh. But rotates counterclockwise with respect to guide rails 2'. Medial cross-member 1' also pivots with respect to the guide rails and the forces which were present when the leg was extended are now absent. However, due to the pivoting of the cross-members, brace B' still remains in close contact with the patient's leg, so that no unsightly bulge would be visible beneath the patient's clothing. In particular, guide rails 2' are in intimate contact with the patient's leg, so that support for lateral stabilization of the leg is provided at all times (i.e. whether the leg is flexed or extended).

Although specific embodiments of the invention have been disclosed for illustrative purposes, it will be appreciated by those skilled in the art that many additions, modifications and substitutions are possible without departing from the scope and spirit of the invention as defined by the accompanying claims.

What is claimed is:

1. A brace for application on a patient's leg in a predetermined worn position to stabilize the knee joint and prevent knee strain while permitting normal movement of the leg, comprising:
   a pair of substantially rigid, opposed guide rail means, each having an upper and lower end, for extending substantially above and below the patient's knee joint on either side of the leg;
   a substantially rigid upper cross-member mounted near the upper end of each guide rail and positioned to extend across and engage the front of the patient's leg at a point above the knee joint;
   a medial cross-member mounted to each of said guide rails below said upper cross-member and positioned to extend across and engage the rear of the patient's leg in the vicinity of the knee joint for providing a forwardly directed supporting force therefor; and
   an inelastic lower cross-member mounted to each of said guide rails near the lower end thereof and positioned to extend across and engage the front of the patient's leg at a point below the knee joint;
   at least one of said cross-members being at least partially detachable to permit application and removal of the knee brace on the patient's leg, one of said upper and medial cross-members being mounted for pivotal movement with respect to said guide rails so that said one cross-member pivots to conform said knee brace to the patient's leg as he bends and extends the same.

2. A knee brace in accordance with claim 1 wherein said guide rails are shaped to follow the general profile of the patient's leg.

3. A knee brace in accordance with claim 1 wherein said guide rails are fitted in intimate contact at the sides of the patient's leg, thereby providing lateral stabilization of the knee joint.

4. A knee brace in accordance with claim 3 wherein said guide rails bow outwardly and away from the patient's leg in the vicinity of the knee joint and are thereby adapted to accommodate a swelled joint.

5. A knee brace in accordance with claim 1 wherein said upper cross-member is shaped to conform to the contour of the front of the patient's thigh and is mounted on each of said guide rails.

6. A knee brace in accordance with claim 1 wherein said medial cross-member is shaped to conform to the contour of the rear of the patient's leg in the vicinity of the knee joint and is mounted for pivotal movement with respect to said guide rails.

7. A knee brace in accordance with claim 1 wherein said lower cross-member is detachable to permit application and removal of said knee brace.

8. A knee brace in accordance with claim 7 wherein said lower cross-member is a flexible strap, at least one of said guide rails having a strap-receiving loop mounting said strap thereto, said strap extending through said loop and being fastened so as to fold back on itself to secure the brace on the patient's leg, said strap including releasable means for retaining said strap in its folded back position.

9. A knee brace in accordance with claim 8 wherein said releasable means comprises complementary mating surfaces on said strap so that the same is continuously adjustable.

10. A knee brace in accordance with claim 1, further comprising eleastic means having first and second ends secured at opposed points on a substantially rigid upper cross-member, said elastic means extending across the rear of the patient's thigh and cooperating with said upper cross-member to form a closed elastic loop extending around the patient's thigh, so that said knee brace is retained on the patient's thigh without slipping therealong.

11. A knee brace in accordance with claim 10 wherein each of said opposed points is spaced from a point at which the upper cross-member is secured to a corresponding one of said guide rails.

12. A knee brace in accordance with claim 1 wherein said medial cross-member is mounted for pivotal movement with respect to said guide rails.

13. A method for stabilizing the knee joint on a patient's leg to prevent knee strain while permitting normal movement of the leg, said method being performed with the aid of a brace to be worn on the patient's leg and comprising a pair of opposed guide rails, each having an upper and lower end, a substantially rigid upper cross-member mounted near the upper end of each guide rail, an inelastic lower cross-member mounted to each guide rail near the lower end thereof, and a medial cross-member mounted to each of said guide rails between said upper and lower cross-members, at least one of said cross-members being at least partially detachable to permit application and removal of the knee brace on the patient's leg, and one of said cross-members being mounted for pivotal movement with respect to said guide rails, said method comprising the steps of:

detaching at least one of said detachable cross-members;

placing the brace on the patient's leg with said upper cross-member extending across the leg at a point above the knee joint, said medial cross-member extending across the rear of the leg in the vicinity of the knee joint and said lower cross-member extending across the front of the leg at a point below the knee joint;

with the patient's leg in its maximally extended position, securing said detached cross-members to place all cross-members in engagement with the patient's leg;

said knee brace stabilizing the knee joint and permitting normal bending and straightening thereof, said pivotally mounted cross-member permitting said knee brace to conform closely to said leg while bending and straightening the same.

* * * * *